(12) United States Patent
Hufnagel et al.

(10) Patent No.: US 9,301,691 B2
(45) Date of Patent: Apr. 5, 2016

(54) INSTRUMENT FOR OPTICALLY DETECTING TISSUE ATTRIBUTES

(71) Applicant: Covidien LP, Mansfield, MA (US)

(72) Inventors: Elizabeth Hufnagel, Boulder, CO (US); Xingrui Chen, Glastonbury, CT (US); Matthew Chowaniec, Middletown, CT (US); Peter T. Collings, Shelton, CT (US); Paul D. Richard, Shelton, CT (US); Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 29 days.

(21) Appl. No.: 14/516,812

(22) Filed: Oct. 17, 2014

(65) Prior Publication Data
US 2015/0238088 A1    Aug. 27, 2015

Related U.S. Application Data (60) Provisional application No. 61/942,937, filed on Feb. 21, 2014.

(51) Int. Cl.
*A61B 5/00* (2006.01)
*A61B 1/00* (2006.01)
(Continued)

(52) U.S. Cl.
CPC .......... *A61B 5/0084* (2013.01); *A61B 1/00004* (2013.01); *A61B 1/00055* (2013.01);
(Continued)

(58) Field of Classification Search
CPC ............ A61B 17/068; A61B 19/2203; A61B 1/00004; A61B 1/00055; A61B 1/00087; A61B 2017/00057; A61B 2018/00785; A61B 2505/05; A61B 5/0084; A61B 5/1075; A61B 5/6847

See application file for complete search history.

(56) References Cited

U.S. PATENT DOCUMENTS 2,777,340 A    1/1957   Hettwer et al.
2,957,353 A   10/1960   Babacz
(Continued)

FOREIGN PATENT DOCUMENTS

AU    2008229795 A1    4/2009
CA      2451558 A1    1/2003
(Continued)

OTHER PUBLICATIONS

European Search Report dated Aug. 3, 2015, issued in European Application No. 14199775.
(Continued)

*Primary Examiner* — Mark Remaly (57) ABSTRACT

A jaw assembly including first and second jaw members configured to clamp tissue therebetween. The first jaw member includes a surface opposing a surface of the second jaw member, a light source, and a light detector. The light source is configured to emit light from an opening defined in the surface of the first jaw member. The light detector is disposed within the opening and is configured to sense properties of light reflected off tissue clamped between the first and second jaw members and to generate signals indicative of the sensed properties of light. A processor is operatively associated with the light detector and is configured to receive the signals from the light detector. The processor is also configured to analyze the signals to determine an attribute of tissue clamped between the first and second jaw members and to provide feedback to a user of the attribute of the tissue.

21 Claims, 6 Drawing Sheets

(51) Int. Cl.
*A61B 17/068* (2006.01)
*A61B 5/107* (2006.01)
*A61B 19/00* (2006.01)
*A61B 17/00* (2006.01)
*A61B 18/00* (2006.01)

(52) U.S. Cl.
CPC ........... *A61B1/00087* (2013.01); *A61B 5/1075* (2013.01); *A61B 5/6847* (2013.01); *A61B 17/068* (2013.01); *A61B 19/2203* (2013.01); *A61B 2017/00057* (2013.01); *A61B 2018/00785* (2013.01); *A61B 2505/05* (2013.01)

(56) References Cited

U.S. PATENT DOCUMENTS

| | | | |
|---|---|---|---|
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,162,399 | A | 7/1979 | Hudson |
| 4,606,343 | A | 8/1986 | Conta et al. |
| 4,705,038 | A | 11/1987 | Sjostrom et al. |
| 4,722,685 | A | 2/1988 | de Estrada et al. |
| 4,823,807 | A | 4/1989 | Russell et al. |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |
| 5,280,788 | A | 1/1994 | Janes et al. |
| 5,301,061 | A | 4/1994 | Nakada et al. |
| 5,312,023 | A | 5/1994 | Green et al. |
| 5,326,013 | A | 7/1994 | Green et al. |
| 5,350,355 | A | 9/1994 | Sklar |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,411,508 | A | 5/1995 | Bessler et al. |
| 5,413,267 | A | 5/1995 | Solyntjes et al. |
| 5,427,087 | A | 6/1995 | Ito et al. |
| 5,467,911 | A | 11/1995 | Tsuruta et al. |
| 5,476,379 | A | 12/1995 | Disel |
| 5,487,499 | A | 1/1996 | Sorrentino et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,540,375 | A | 7/1996 | Bolanos et al. |
| 5,540,706 | A | 7/1996 | Aust et al. |
| 5,542,594 | A | 8/1996 | McKean et al. |
| 5,562,239 | A | 10/1996 | Boiarski et al. |
| 5,632,432 | A | 5/1997 | Schulze et al. |
| 5,653,374 | A | 8/1997 | Young et al. |
| 5,658,300 | A | 8/1997 | Bito et al. |
| 5,667,517 | A | 9/1997 | Hooven |
| 5,693,042 | A | 12/1997 | Boiarski et al. |
| 5,704,534 | A | 1/1998 | Huitema et al. |
| 5,713,505 | A | 2/1998 | Huitema |
| 5,762,603 | A | 6/1998 | Thompson |
| 5,779,130 | A | 7/1998 | Alesi et al. |
| 5,782,396 | A | 7/1998 | Mastri et al. |
| 5,782,397 | A | 7/1998 | Koukline |
| 5,820,009 | A | 10/1998 | Melling et al. |
| 5,863,159 | A | 1/1999 | Lasko |
| 5,908,427 | A | 6/1999 | McKean et al. |
| 5,954,259 | A | 9/1999 | Viola et al. |
| 5,964,774 | A | 10/1999 | McKean et al. |
| 5,993,454 | A | 11/1999 | Longo |
| 6,010,054 | A | 1/2000 | Johnson et al. |
| 6,017,354 | A | 1/2000 | Culp et al. |
| 6,032,849 | A | 3/2000 | Mastri et al. |
| 6,045,560 | A | 4/2000 | McKean et al. |
| 6,090,123 | A | 7/2000 | Culp et al. |
| 6,126,651 | A | 10/2000 | Mayer |
| 6,129,547 | A | 10/2000 | Cise et al. |
| 6,239,732 | B1 | 5/2001 | Cusey |
| 6,241,139 | B1 | 6/2001 | Milliman et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,371,909 | B1 | 4/2002 | Hoeg et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,533,157 | B1 | 3/2003 | Whitman |
| 6,537,280 | B2 | 3/2003 | Dinger et al. |
| 6,610,066 | B2 | 8/2003 | Dinger et al. |
| 6,611,793 | B1 | 8/2003 | Burnside et al. |
| 6,645,218 | B1 | 11/2003 | Cassidy et al. |
| 6,654,999 | B2 | 12/2003 | Stoddard et al. |
| 6,698,643 | B2 | 3/2004 | Whitman |
| 6,699,177 | B1 | 3/2004 | Wang et al. |
| 6,716,233 | B1 | 4/2004 | Whitman |
| 6,783,533 | B2 | 8/2004 | Green et al. |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 | 12/2004 | Hillstead et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 7,032,798 | B2 | 4/2006 | Whitman et al. |
| RE39,152 | E | 6/2006 | Aust et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,111,769 | B2 | 9/2006 | Wales et al. |
| 7,122,029 | B2 | 10/2006 | Koop et al. |
| 7,140,528 | B2 | 11/2006 | Shelton, IV |
| 7,143,923 | B2 | 12/2006 | Shelton, IV et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,172,104 | B2 | 2/2007 | Scirica et al. |
| 7,225,964 | B2 | 6/2007 | Mastri et al. |
| 7,238,021 | B1 | 7/2007 | Johnson |
| 7,246,734 | B2 | 7/2007 | Shelton, IV |
| 7,328,828 | B2 | 2/2008 | Ortiz et al. |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,422,139 | B2 | 9/2008 | Shelton, IV et al. |
| 7,431,189 | B2 | 10/2008 | Shelton, IV et al. |
| 7,441,684 | B2 | 10/2008 | Shelton, IV et al. |
| 7,448,525 | B2 | 11/2008 | Shelton, IV et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,481,347 | B2 | 1/2009 | Roy |
| 7,481,824 | B2 | 1/2009 | Boudreaux et al. |
| 7,487,899 | B2 | 2/2009 | Shelton, IV et al. |

(56) References Cited

U.S. PATENT DOCUMENTS

| | | |
|---|---|---|
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,787,129 B2 | 8/2010 | Zysk et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,170,649 B2 | 5/2012 | Johansson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 2003/0038938 A1 | 2/2003 | Jung et al. |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0278680 A1 | 12/2006 | Viola et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0198080 A1 | 8/2010 | Liu et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0214025 A1 | 8/2013 | Zemlok et al. |

(56) References Cited

U.S. PATENT DOCUMENTS

| | | |
|---|---|---|
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2676615 A2 | 12/2013 |
| ES | 2333509 A1 | 2/2010 |
| JP | 08-038488 | 2/1996 |
| JP | 2005-125075 A | 5/2005 |
| WO | 99/15086 A1 | 4/1999 |
| WO | 00/72760 A1 | 12/2000 |
| WO | 00/72765 A1 | 12/2000 |
| WO | 03/000138 A2 | 1/2003 |
| WO | 03/026511 A1 | 4/2003 |
| WO | 03/030743 A2 | 4/2003 |
| WO | 03065916 A1 | 8/2003 |
| WO | 03/077769 A1 | 9/2003 |
| WO | 03090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008112147 A1 | 9/2008 |
| WO | 2008/131362 A2 | 10/2008 |
| WO | 2008/133956 A2 | 11/2008 |
| WO | 2009005850 A1 | 1/2009 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |
| WO | 2012099974 A2 | 7/2012 |
| WO | 2013148054 A1 | 10/2013 |

OTHER PUBLICATIONS

Extended European Search Report corresponding to EP No. 11 17 8021.9, mailed Jun. 4, 2013; (3 pp).

Extended European Search Report corresponding to EP No. 13 16 3033.7, completed Jun. 27, 2013 and mailed Jul. 15, 2013; (8 pp.).

Extended European Search Report corresponding to EP No. 12 18 6177.7, completed Aug. 14, 2013 and mailed Aug. 23, 2013; (8 pp.).

Partial European Search Report corresponding to EP No. 13 17 1742.3, completed Sep. 17, 2013 and mailed Sep. 25, 2013; (8 pp.).

Partial European Search Report corresponding to EP No. 13 17 2400.7, completed Sep. 18, 2013 and mailed Oct. 1, 2013; (7 pp.).

Extended European Search Report corresponding to EP No. 13 17 5475.6, completed Sep. 23, 2013 and mailed Oct. 1, 2013; (8 pp.).

Extended European Search Report corresponding to EP No. 13 17 5478.0, completed Sep. 24, 2013 and mailed Oct. 2, 2013; (6 pp.).

Extended European Search Report corresponding to EP No. 13 17 5479.8, completed Sep. 27, 2013 and mailed Oct. 10, 2013; (7 pp.).

Partial Extended European Search Report corresponding to EP 13 17 5477.2, completed Oct. 7, 2013 and mailed Oct. 15, 2013; (7 pp.).

Extended European Search Report corresponding to EP No. 08 25 2703.7, completed Oct. 23, 2008 and mailed Oct. 31, 2008; (7 pp.).

International Search Report corresponding to PCT/US2005/027266, completed May 30, 2008 and mailed Jun. 18, 2008; (2 pp.).

Extended European Search Report corresponding to EP 08 25 2703.7, completed Oct. 23, 2008 and mailed Oct. 31, 2008; (7 pp.).

Extended European Search Report corresponding to EP 08 25 3184.9, completed Feb. 12, 2009 and mailed Feb. 27, 2009; (3 pp.).

Extended European Search Report corresponding to EP 10 25 0228.3, completed May 20, 2010 and mailed Jun. 1, 2010; (6 pp.).

Extended European Search Report corresponding to EP 10 25 2037.6, completed Mar. 1, 2011 and mailed Mar. 9, 2011; (3 pp.).

Extended European Search Report corresponding to EP 10 25 1968.3, completed on Jul. 4, 2011 and mailed Jul. 14, 2011; (12 pp.).

Extended European Search Report corresponding to EP 11 15 2266.0, completed Jul. 15, 2011 and mailed Jul. 28, 2011; (3 pp.).

Extended European Search Report corresponding to EP 11 25 0462.6, completed Jul. 20, 2011 and mailed Jul. 28, 2011; (6 pp.).

Extended European Search Report corresponding to EP 11 25 0771.0, completed Feb. 7, 2012 and mailed Feb. 17, 2012; (3 pp.).

Extended European Search Report corresponding to EP 06 78 8914.7, completed May 3, 2012 and mailed May 11, 2012; (8 pp.).

Partial European Search Report corresponding to EP 12 18 6177.7, completed Jan. 30, 2013 and mailed Feb. 12, 2013; (6 pp.).

European search Report from Appl. No. 13177163.6 dated Nov. 15, 2013. (8 pp).

Extended European Search Report from EP Application No. 13172400.7 dated Jan. 21, 2014.

Extended European Search Report from EP Application No. 13189026.1 dated Jan. 31, 2014.

(56) References Cited

OTHER PUBLICATIONS

The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
European Search Report No. 13189650.8 dated Sep. 10, 2014.

INSTRUMENT FOR OPTICALLY DETECTING TISSUE ATTRIBUTES

CROSS-REFERENCE TO RELATED APPLICATIONS

This application claims the benefit of and priority to U.S. Provisional Patent Application No. 61/942,937, filed Feb. 21, 2014, the entire disclosure of which is incorporated by reference herein.

BACKGROUND

1. Technical Field

The present disclosure relates to surgical instruments and, more specifically, to a surgical instrument for detecting attributes of tissue with optical technology.

2. Discussion of Related Art

In endoscopic surgical procedures, surgery is performed in any hollow viscus of the body through a small incision or through narrow endoscopic tubes (cannulas) inserted through a small entrance wound in the skin or through a naturally occurring orifice. Endoscopic surgical procedures performed within the interior of the abdomen are referred to as laparoscopic procedures. As used herein both laparoscopic and endoscopic procedures will be collectively referred to as endoscopic procedures. Endoscopic procedures often require the clinician to act on organs, tissues and vessels far removed from the incision During endoscopic procedures, a surgeon may benefit from knowing attributes of tissue being manipulated to increase the effectiveness of the procedure. For example, knowing the thickness of tissue may aid a surgeon in selecting the proper size staple for the tissue. In addition, identifying the vascular properties within the surgical site the surgeon may identify the red blood cell concentration to determine whether the tissue is diseased or cancerous.

SUMMARY

Accordingly, the present disclosure relates to an endoscopic surgical instrument configured to provide intraoperative feedback of tissue properties within a surgical site.

In an aspect of the present disclosure, a jaw assembly includes first and second jaw members moveable relative to one another between an open configuration and a clamped configuration. In the clamped configuration, the first and second jaw members are configured to clamp tissue therebetween. The first jaw member includes a surface opposing a surface of the second jaw member. The first jaw member further includes an opening defined in the surface of the first jaw member. The first jaw member also includes a light source configured to emit light from the opening and a light detector disposed within the opening. The light detector is configured to sense properties of light reflected off tissue clamped between the first and second jaw members and to generate signals indicative of the sensed properties of light. The jaw assembly further includes a processor operatively associated with the light detector. The processor is configured to receive signals indicative of properties of light from the light detector, to analyze the signals to determine an attribute of tissue clamped between the first and second jaw members, and to provide auditory, haptic, or visual feedback to a user of the attribute of the tissue. The processor may be configured to determine a thickness of tissue clamped between the first and second jaw members. The light source may be configured to generate light by one of electron-stimulation, incandescent lamps, light emitting diodes, electroluminescence, gas discharge, high-intensity discharge, laser, chemoluminescence, fluorescence, or phosphorescence.

In embodiments, the second jaw member includes a second light detector disposed within a second opening defined in the surface of the second jaw member. The second light detector is configured to sense properties of light transmitted through tissue clamped between the first and second jaw members from the light source of the first jaw member and transmitted and to generate signals indicative of the sensed properties of light. The second light detector may transmit the signals to the processor.

In some embodiments, the second jaw member includes a second light source configured to emit light through a second opening defined in the surface of the second jaw member. The second jaw member further includes a second light detector disposed within the second opening configured to sense properties of light emitted from the second light source and reflected off tissue clamped between the first and second jaw members and to generate signals indicative of the sensed properties of light.

In certain embodiments, the first jaw member includes an anvil and the second jaw member includes a staple cartridge. The staple cartridge includes a plurality of staples configured to be driven through tissue clamped between the first and second jaw members.

In aspects of the present disclosure, a surgical instrument includes a handle, an elongated shaft extending from the handle, and a jaw assembly. The jaw assembly includes first and second jaw members moveable relative to one another between an open configuration and a clamped configuration. In the clamped configuration, the first and second jaw members are configured to clamp tissue therebetween. The first jaw member includes a surface opposing a surface of the second jaw member. The first jaw member further includes an opening defined in the surface of the first jaw member. The first jaw member also includes a light source configured to emit light from the opening and a light detector disposed within the opening. The light detector is configured to sense properties of light reflected off tissue clamped between the first and second jaw members and to generate signals indicative of the sensed properties of light. The jaw assembly further includes a processor operatively associated with the light detector. The processor is configured to receive signals indicative of properties of light from the light detector, to analyze the signals to determine an attribute of tissue clamped between the first and second jaw members, and to provide auditory, haptic, or visual feedback to a user of the attribute of the tissue.

In embodiments, the surgical instrument may include a control interface disposed on the handle that is operatively associated with the jaw assembly. The control interface is configured to actuate the first and second jaw members between the open and clamped configurations. The control interface is operatively associated with the light source to activate the light source to emit light from the opening.

In some embodiments, the surgical instrument includes a display panel disposed on the handle. The display panel operatively associated with the processor and configured to display feedback of the attribute of the tissue.

In certain embodiments, the processor is disposed within the elongated shaft. In other embodiments, the processor is disposed within the handle.

In particular embodiments, one of jaw members includes a staple cartridge having a plurality of staples configured to fire through tissue clamped between the first and second jaw members. The processor may be configured to control the firing of staples from the surgical instrument.

In some aspects of the present disclosure, a method for detecting tissue attributes includes providing a jaw assembly, clamping tissue between first and second jaw members of the jaw assembly, emitting light from an opening in a surface of the first jaw member, sensing properties of light reflected of the tissue, transmitting signals indicative of properties of light to a processor, determining tissue attributes from the signals with the processor, and providing feedback of the tissue attributes to a user. The first and second jaw members are moveable relative to one another between an open configuration and a clamped configuration. The surface of the first jaw member opposes the second jaw member.

The method may include sensing properties of light transmitted through the tissue clamped between the first and second jaw members of the jaw assembly. The first jaw member including a light source and the second jaw member including a second light detector. Emitting light from the opening may include activating a light source of the first jaw member.

The method may include firing staples from a staple cartridge coupled to one of the first and second jaw members through tissue clamped between the first and second jaw members. Determining tissue attributes may include determining tissue thickness of tissue clamped between the jaw members and the method may include comparing the determined tissue thickness to a predetermined tissue thickness value and preventing additional functions of the surgical instrument when the determined tissue thickness is greater than the predetermined value. The method may further include inputting the predetermined tissue thickness value into a control interface operatively associated with the processor. The method may further include coupling the staple cartridge to one of the first and second jaw members. The staple cartridge may transmit the predetermined value to the processor.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

Figure 1:
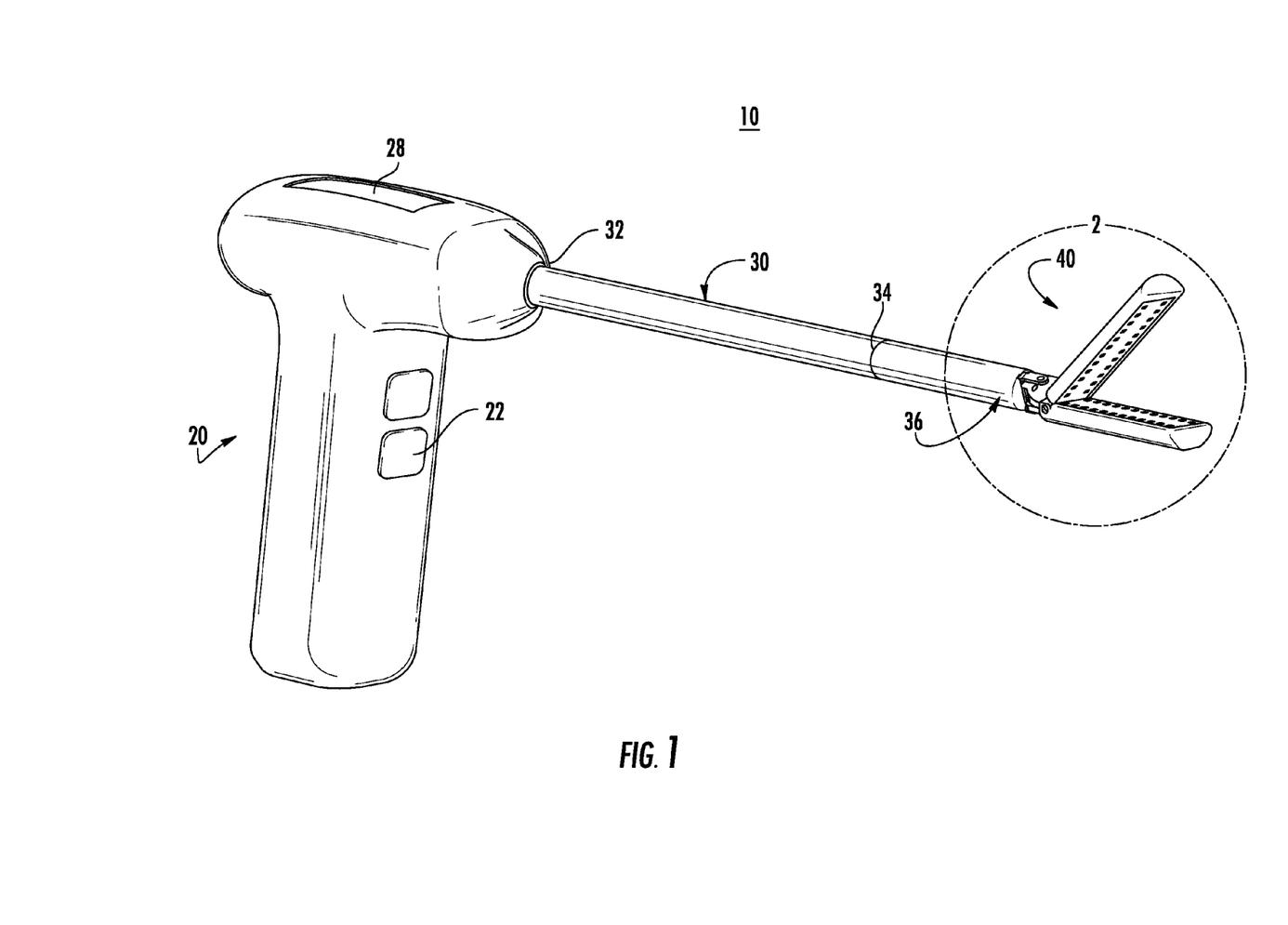
FIG. 1 is a perspective view of a surgical instrument in accordance with the present disclosure including an end effector configured to optically detect properties of tissue.

Referring to FIG. 1, a surgical instrument 10 is provided in accordance with the present disclosure including a handle 20, an elongated shaft 30 extending from the handle 20, and a jaw assembly 40 coupled to a distal end 34 of the elongated shaft 30. The handle 20 includes a control interface 22 and a display panel 28. The control interface 22 is operatively associated with the jaw assembly 40 as detailed below. The display panel 28 is configured to display tissue properties of tissue clamped within the jaw assembly 40 as detailed below.

In alternate embodiments, the display panel 28 is not present on the handle 20 but rather is or functions as a screen remote to the surgical instrument 10 (e.g., a surgical monitor (not shown) inside or outside an operating theater). It is contemplated that the control interface 22 may be integrated into the display panel 28 (e.g., a touch screen display panel whether the display panel 28 is on the handle 20 or remote).

In embodiments, the handle 20 is a powered handle and the control interface 22 includes a plurality of buttons or switches to manipulate the jaw assembly 40. In some embodiments, the handle 20 is a manual handle and the control interface 22 includes triggers and levers (not shown) to manipulate the jaw assembly 40. An exemplary example of such a handle is disclosed in commonly owned and co-pending U.S. patent application Ser. No. 13/484,975, filed May 31, 2012, published as U.S. Patent Publication No. 2012/0253329 on Oct. 4, 2012, the contents of which is hereby incorporated by reference in its entirety.

The elongated shaft 30 operatively associates the jaw assembly 40 with the handle 20. A proximal end 32 of the elongated shaft 30 may be integrally formed with the handle 20. In embodiments, the proximal end 32 releasably couples the elongated shaft 30 to the handle 20. In some embodiments, the distal end 34 of the elongated shaft 30 includes a detachable end effector assembly 36 including the jaw assembly 40. In embodiments, the elongated shaft 30 may rotate relative to the handle 20. In some embodiments, the jaw assembly 40 articulates relative to the elongated shaft 20.

Figure 2:
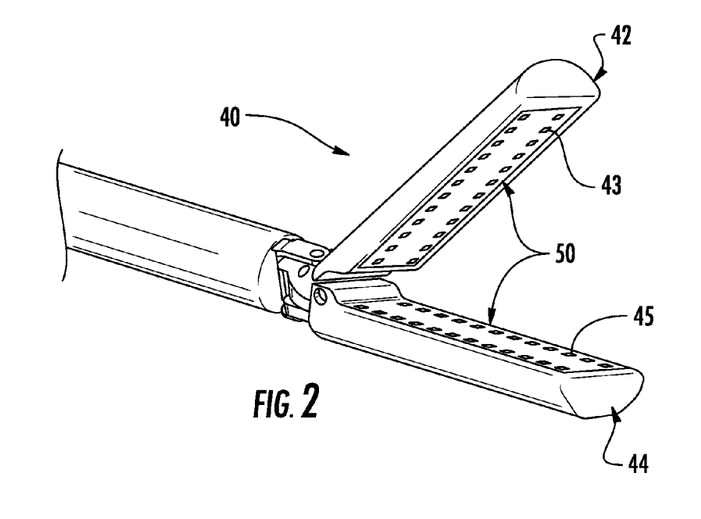
FIG. 2 is an enlargement of the detail area "2" of FIG. 1 showing the jaw members of the surgical instrument of FIG. 1 in an open configuration.
Figure 3:
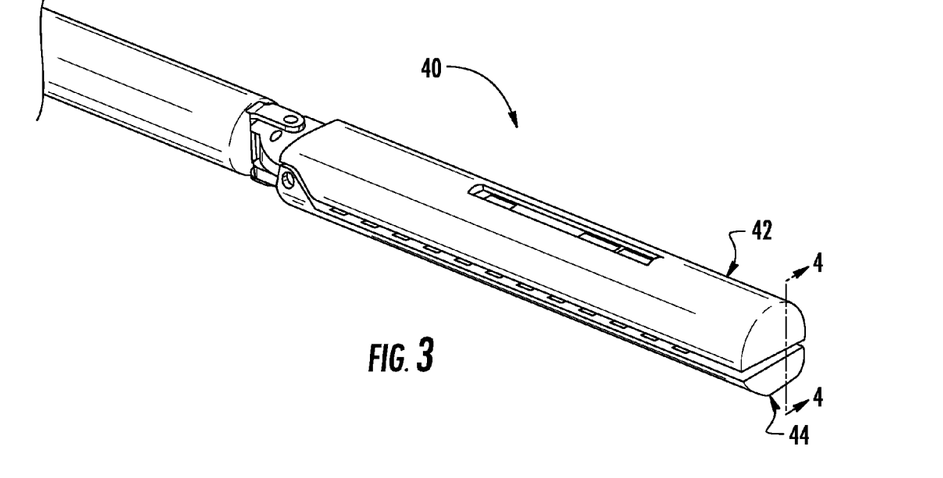
FIG. 3 is a perspective view of the jaw members of FIG. 2 in a clamped configuration.
Figure 4:
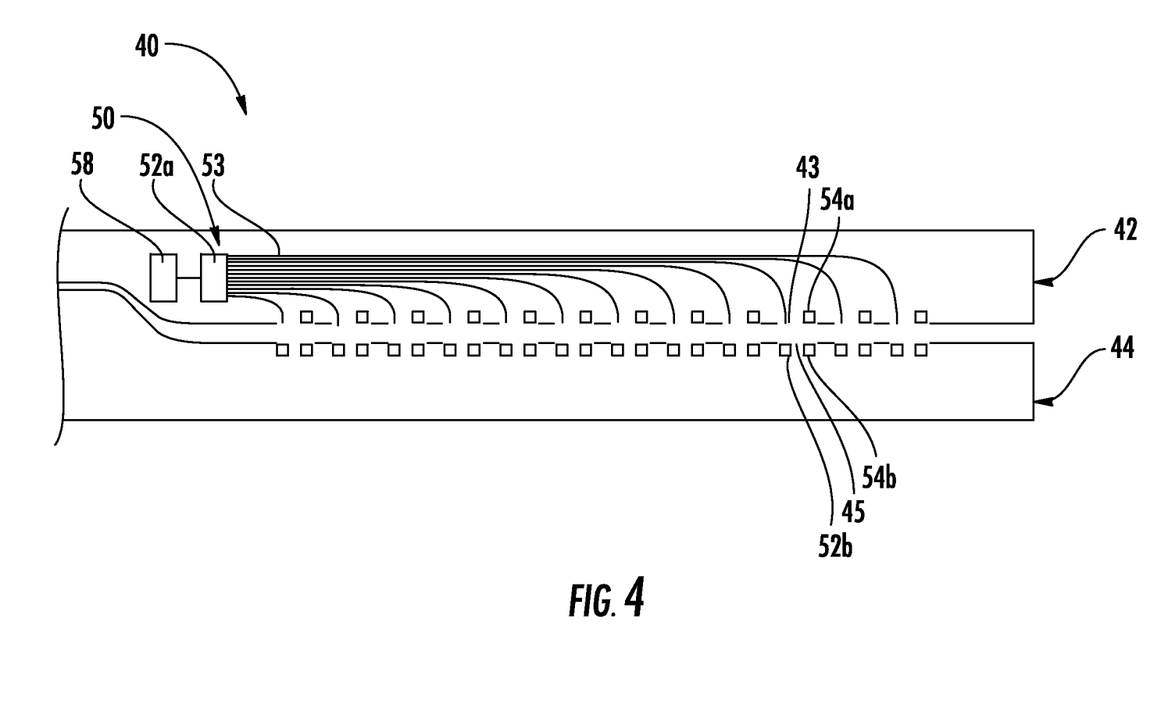
FIG. 4 is a side cross-sectional view taken along the line 4-4 of FIG. 3, illustrating the components of a detection assembly.

With reference to FIGS. 2-4, the jaw assembly 40 includes an upper jaw member 42, a lower jaw member 44, and a detection assembly 50. The upper jaw member 42 defines a plurality of openings 43 in a surface opposing the lower jaw member 44. The lower jaw member 44 may define a plurality of openings 45 in a surface 43 opposing the upper jaw member 42.

The jaw members 42, 44 are moveable relative to one another between an open configuration (FIG. 2), wherein the jaw members 42, 44 are spaced-apart from one another, and a clamped configuration (FIG. 3), wherein the jaw members 42, 44 are approximated. The control interface 22 (FIG. 1) may be used to command a transition of the jaw members 42, 44 between the open and clamped configurations.

With particular reference to FIG. 4, the detection assembly 50 is disposed within the jaw assembly 40 and includes light sources 52a, 52b, light detectors 54a, 54b, and a processor 58. The upper jaw member 42 includes a single light source 52a and a light detector 54a disposed within each opening 43 defined by the upper jaw member 42. Light from the light source 52a is guided to each opening 43 through fiber optic cables or light pipes 53 such that light from light source 52a is emitted from each of the openings 43. It will be appreciated that having the light sources and the light detectors in a single jaw member (e.g., upper jaw member 42) simplifies the routing of wiring and cables to the light sources and the light detectors. In addition, it will be appreciated that the single jaw member may be fixed relative to the elongated shaft to further simplify the routing of wiring and cables to the light sources and the light detectors.

In embodiments, the lower jaw member 44 includes a plurality of light sources 52b and light detectors 54b disposed within each opening 45 defined by the lower jaw member 44. The light sources 52b are direct light sources configured to emit light through openings 45.

The light source 52a, 52b may generate light by a variety of means including but not limited to electron-stimulation, incandescent lamps, electroluminescent, gas discharge, high-intensity discharge, lasers, chemoluminescence, fluorescence, and/or phosphorescence. It is contemplated that the lower jaw member 44 may include a single light source 52b guided through fiber optic cables or light pipes (not shown), to openings 45, similar to the fiber optic cables or light pipes 53 extending through the upper jaw member 42 to the openings 43. It is further contemplated that the light source 52a may be a plurality of light sources 52a disposed within openings 43 of the upper jaw member 42, similar to light sources 52b disposed within the openings 45 of the lower jaw member 44.

Each light detector 54a, 54b is operatively associated with the processor 58. Each light detector 54a, 54b is a sensor configured to optically sense properties of light contacting the light detector 54a, 54b. Each light detector 54a, 54b is operatively associated with the processor 58. It is contemplated that each light detector 54a, 54b may be wired directly to or wirelessly connected to the processor 58. It is within the scope of this disclosure that light detectors 54a, 54b are tuned to one another to enhance the detection of light attributes. It is also within the scope of this disclosure that each light source, each light pipe, or each a group of light sources or light pipes may be associated with a specific light detector such that the light detector is configured to only detect light from the associated light source, light pipe, or group of light sources or light pipes. Further, it is within the scope of this disclosure that the light sources or light pipes may be operated sequentially to produce a clearer image of the tissue properties.

The wireless connection may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

The processor 58 may be disposed within the surgical instrument 10 (e.g., within the handle 20, the elongate shaft 30, or the jaw assembly 40) or external to the surgical instrument 10. The processor 58 is configured to receive one or more signal(s) including properties of light from the light detectors 54a, 54b and is configured to analyze the signal(s) to determine an attribute of tissue clamped between the first and second jaw members. The processor 58 is operatively associated with the display panel 28 to display the attribute of tissue clamped within the jaw assembly 40 as detailed below.

Each light detector 54a, 54b may be configured to detect a specific chemical or agent injected into the blood stream of a patient including but not limited to chemicals or agents cable of bioluminescence, radioluminescence, chemoluminescence, fluorescence, and/or phosphorescence. It is contemplated that each light detector 54a, 54b may be configured to detect the same or different chemicals or agents than each other light detector 54a, 54b. It is also contemplated that each opening 43, 45 in a respective one of the jaw members 42, 44 may include more than one light detector 54a, 54b with each light detector 54a, 54b configured to sense a different or the same attribute of light.

With reference to FIGS. 3 and 4, the detection assembly 50 is used to determine the attributes of tissue clamped within the jaw assembly 40 in accordance with the present disclosure. When tissue is clamped between the upper and lower jaw members 42, 44 of the jaw assembly 40 one or more of the light sources 52a, 52b is activated to emit light from respective openings 43, 45 in the jaw members 42, 44. The control assembly 22 (FIG. 1) may be used to activate the light sources 52a, 52b. The light emitted from the openings 43, 45 is reflected off the surface of the tissue clamped within the jaw assembly 40, backscattering some light back into respective openings 43, 45 (e.g., light emitted from the light source 52a through an opening 43 reflects off the surface of tissue, travels back into the opening 43 and is sensed by the light detector 54a disposed within the opening 43). The light may also be transmitted through the tissue and into an opposing opening 43, 45 (e.g., light emitted from the light source 52a through an opening 43 may be transmitted through the tissue into an opening 45 opposing the opening 43 and sensed by the light detector 54b disposed within the opening 45).

In embodiments, the light sources 52b or the end of the fiber optic cables 53, may be positioned within opening 45 so as to be in direct contact with the surface of tissue to achieve a short photon path length.

The properties of the light sensed by the light detectors 54a, 54b are converted to electrical signals and transmitted to the processor 58. The processor 58 analyzes the signals indicative of the properties of the sensed light to determine attributes of the tissue clamped between the jaw members 42, 44 and displays the tissue attributes on the display panel 28. For example, the intensity of the light may be used to calculate the thickness of known tissue type (i.e., lung, stomach, intestinal, muscular, etc.) clamped within the jaw assembly 40 and the display panel 28 displays the calculated thickness of the tissue.

In addition, the light detectors 54a, 54b may be configured to sense properties of light associated with a specific chemical or agent injected into the blood stream of a patient. Further, the light detectors 54a, 54b may be configured to sense properties of light indicating foreign bodies, diseased tissue, or non-tissue within tissue clamped within the jaw assembly 40.

In embodiments, the processor 58 may compare the tissue thickness of tissue clamped within the jaw assembly 40 to a predetermined value and provide the clinician with indicia that the tissue thickness is greater than or less than the predetermined value. When the tissue thickness is greater than the predetermined value the processor 58 may provide audible, haptic, or visual indicia to the clinician to alert the clinician that the tissue thickness is greater than the predetermined value (e.g., a red light, a failure tone, a stop icon, an alert light pattern, an audible alert pattern, etc.). When the tissue thickness is less than or equal to the predetermined value, the processor 58 may provide audible, haptic, or visual indicia to the clinician to alert the clinician that the tissue thickness is less than or equal to the predetermined value (e.g., a green light, a go ahead tone, a go icon, a go light pattern, an audible go tone, etc.). With a thickness of the tissue determined, a clinician may select an appropriately configured surgical instrument to complete a particular surgical task (e.g., a surgical stapler loaded with an appropriately sized plurality of surgical staples).

Referring to FIGS. 5-8, a surgical instrument 100 is provided in accordance with the present disclosure including a handle 20, an elongated shaft 30 extending from the handle 20, a detachable end effector assembly 36 including a jaw assembly 140. The jaw assembly 140 includes an upper jaw member 142, a lower jaw member 144, and a detection assembly 150. The upper jaw member 142 includes an anvil 162 having a plurality of staple pockets 164. The anvil 162 may be releasably coupled to the upper jaw member 142. An opening 143 is defined in the anvil 162 between each of the staple pockets 164.

Figures 7, 8:
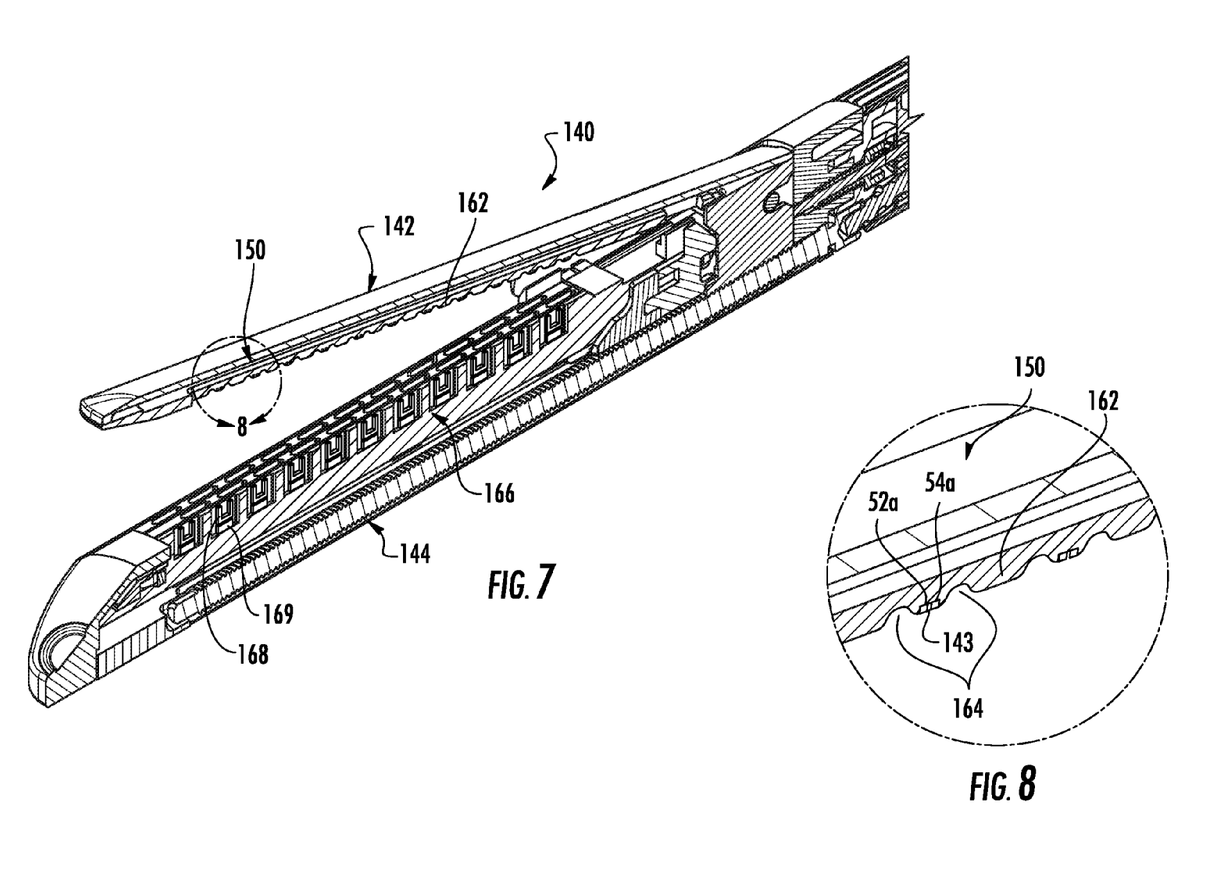
FIG. 7 is a side cross-sectional view taken along the line 7-7 of FIG. 6, illustrating the components of the jaw member assembly.
FIG. 8 is an enlargement of the detail area "8" of FIG. 7 showing a portion of a detection assembly disposed within an opening defined by the upper jaw member.

The lower jaw member 144 includes a staple cartridge 166 having a plurality of staples 168 configured to be fired through tissue clamped between the upper and lower jaw members 142, 144. Each staple 168 is associated with a staple pusher 169 that is configured to urge the staple 168 from the staple cartridge 166, through tissue clamped between the jaw members 142, 144, and towards the anvil 162. When each staple 168 contacts the anvil 162, legs of each staple 168 are formed to secure the staple 168 within the tissue clamped between the jaw members 142, 144. The staple cartridge 166 may be releasably coupled to the lower jaw member 144.

The detection assembly 150 includes a plurality of light sources 52a, a plurality of light detectors 54a, and a processor 158. The light sources 52a and light detectors 54a are disposed within the openings 143 defined in the anvil 162 of the upper jaw member 142. The processor 158 is disposed within the handle 20 and is operatively associated with the light detectors 54a. The light sources 52a, the light detectors 54a, and the processor 158 of surgical instrument 100 operate substantially similar to the light sources 52a, the light detectors 54a, and the processor 58 of surgical instrument 10 detailed above, as such only the differences are detailed below.

The processor 158 may be configured to lock out additional functions of the jaw assembly 140 when the tissue thickness of tissue clamped within the jaw assembly 140 is greater than a predetermined value (e.g., prevents the staples 168 from firing from the staple cartridge 166).

Figure 5:
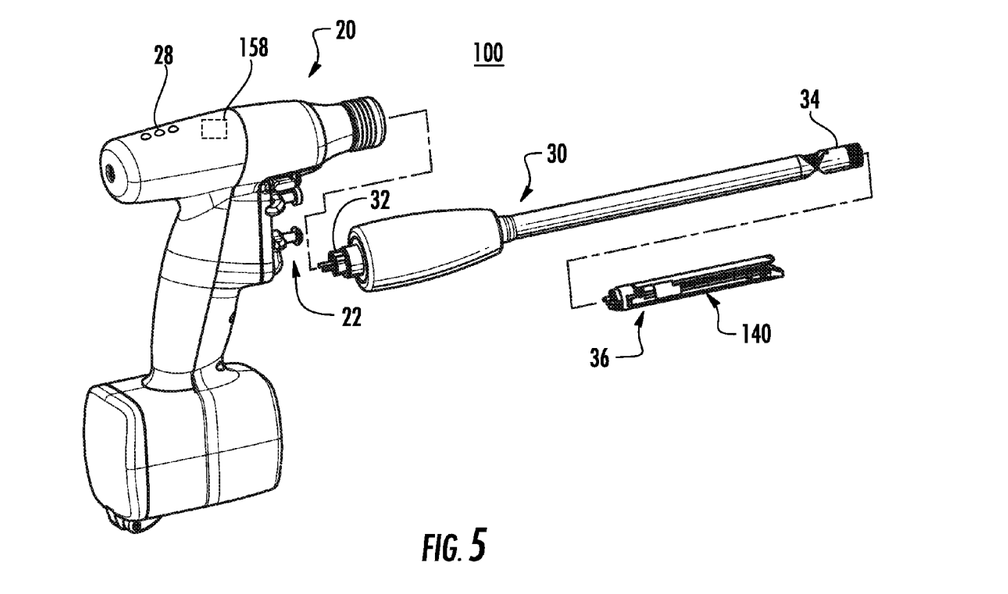
FIG. 5 is a perspective view of a surgical instrument in accordance with the present disclosure including an end effector configured to optically detect properties of tissue and to fire staples through tissue clamped within the end effector.
Figure 6:
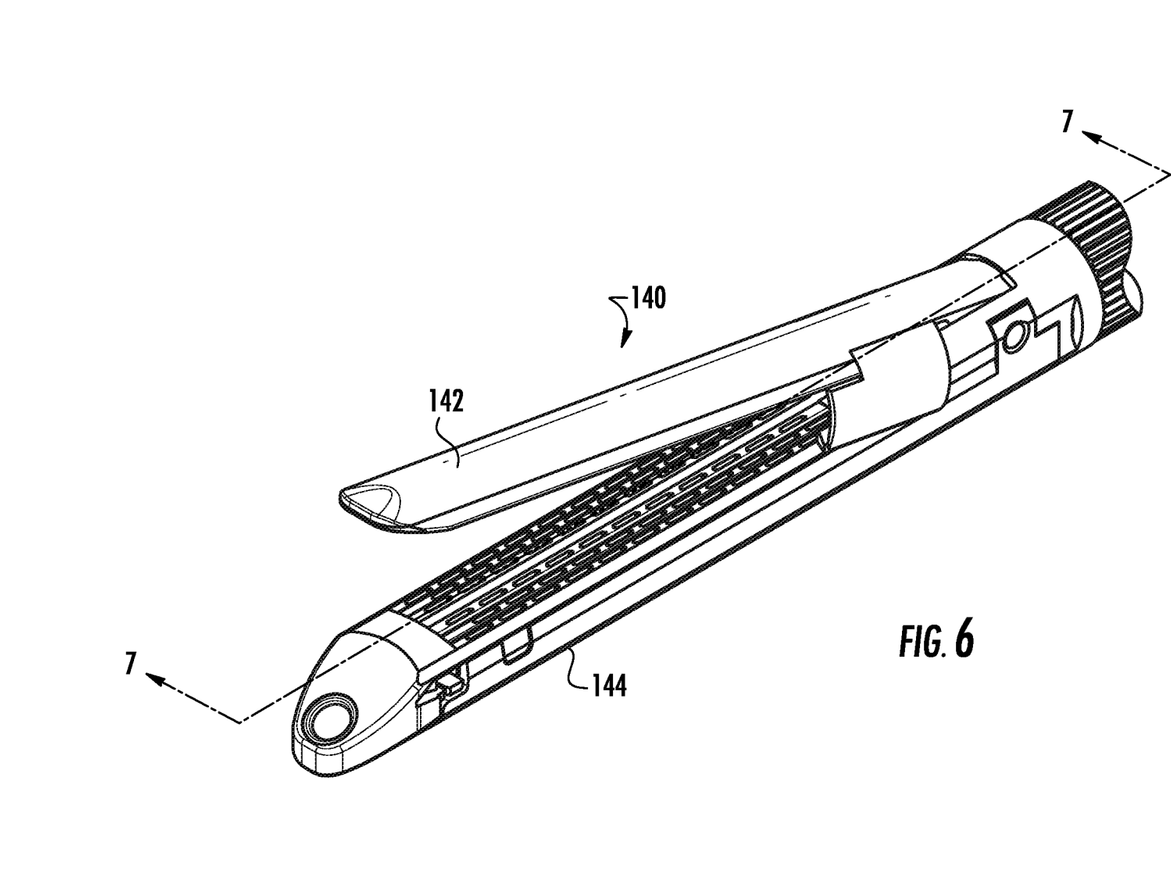
FIG. 6 is a perspective view of the jaw members of the end effector shown in FIG. 5.

The clinician may input the predetermined value into a control assembly 22. The control assembly 22 may be disposed on the handle 20 or remote to the surgical instrument 100. The staple cartridge 166 may be replaceable with a plurality of staple cartridges having varying sized staples 168. The size of the staples 168 within the staple cartridge 166 coupled to the lower jaw member 144 may determine the predetermined value. The staple cartridge 166 may be operatively associated with the processor 158 such that when the staple cartridge 166 is coupled to the lower jaw member 144 the predetermined value associated with the staple cartridge 166 is transmitted to the processor 158. It is also contemplated that the predetermined value includes an upper limit and a lower limit associated with a suitable thicknesses of tissue for the staple cartridge 166 and the processor 158 is configured to prevent the staples 168 from firing if the tissue thickness is not between the upper and lower limits.

The tissue thickness may be determined by the red blood cell density within the tissue. For example, if there is too much blood occlusion the reduced density of the red blood cells indicates that the staples 168 within the staple cartridge 166 are too small for the tissue clamped within the jaw assembly 140.

The attributes of tissue clamped within the jaw member assembly 40, 140 may also be detected by detecting abnormal blood flow. For example, abnormal blood flow may indicate that cancerous or tumorous tissue is clamped within the jaw assembly 40, 140 informing the clinician that a resection margin (i.e., the amount of tissue being removed containing cancerous or tumorous tissue) should be increased.

As mentioned above, the detection assembly 50 may be provided as a standalone instrument or as part of a multifunction surgical instrument including but not limited to a surgical stapler, a grasper, or an electrosurgical device.

The various embodiments disclosed herein may also be configured to work with robotic surgical systems and what is commonly referred to as "Telesurgery". Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein (e.g., the jaw assembly 40) while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions (e.g., tissue resistance due to manipulation, cutting or otherwise treating, pressure by the instrument onto the tissue, tissue temperature, tissue impedance, etc.). As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A jaw assembly comprising:
    first and second jaw members moveable relative to one another between an open configuration and a clamped configuration, the first and second jaw members configured to clamp tissue therebetween in the clamped configuration, the first jaw member including:
        a surface opposing a surface of the second jaw member;
        an opening defined in the surface of the first jaw member;
        a light source configured to emit light from the opening; and
        a light detector disposed within the opening, the light detector configured to sense properties of light reflected off tissue clamped between the first and second jaw members and to generate signals indicative of the sensed properties of light; and
    a processor operatively associated with the light detector, the processor configured to:
        receive signals indicative of properties of light from the light detector;
        analyze the signals to determine an attribute of tissue clamped between the first and second jaw members; and
        provide feedback to a user of the attribute of tissue clamped between the first and second jaw member.

2. The jaw assembly of claim 1, wherein the feedback is at least one of auditory, haptic, or visual.

3. The jaw assembly of claim 1, wherein the processor is configured to determine a thickness of tissue clamped between the first and second jaw members.

4. The jaw assembly of claim 1, wherein the second jaw member includes a second light detector disposed within a second opening defined in the surface of the second jaw member, the second light detector configured to sense properties of light emitted from the light source of the first jaw member and transmitted through tissue clamped between the first and second jaw members, the second light detector operatively associated with the processor.

5. The jaw assembly of claim 1, wherein the second jaw member includes a second light source configured to emit light through a second opening defined in the surface of the second jaw member and includes a second light detector disposed within the second opening, the second light detector configured to sense properties of light emitted from the second light source and reflected off tissue clamped between the first and second jaw members.

6. The jaw assembly of claim 1, wherein the light source is configured to generate light from at least one of electron-stimulation, incandescent lamps, light emitting diodes, electroluminescence, gas discharge, high-intensity discharge, laser, chemoluminescence, fluorescence, or phosphorescence.

7. The jaw assembly of claim 1, wherein the first jaw member includes an anvil and the second jaw member includes a staple cartridge having a plurality of staples configured to be driven through tissue clamped between the first and second jaw members.

8. A surgical instrument comprising:
    a handle;
    an elongated shaft extending from the handle; and
    a jaw assembly coupled to a distal end of the elongated shaft, the jaw assembly including first and second jaw members moveable relative to one another between an open configuration and a clamped configuration, the first and second jaw members configured to clamp tissue therebetween in the clamped configuration, the first jaw member including:
        a surface opposing a surface of the second jaw member;
        an opening defined in the surface of the first jaw member;
        a light source configured to emit light from the opening; and
        a light detector disposed within the opening, the light detector configured to sense properties of light reflected off tissue clamped between the first and second jaw members and to generate signals indicative of the sensed properties of light; and
    a processor operatively associated with the light detector, the processor configured to:
        receive signals indicative of properties of light from the light detector;
        analyze the signals to determine an attribute of tissue clamped between the first and second jaw members; and
        provide feedback to a user of the attribute of the tissue clamped between the first and second jaw member.

9. The surgical instrument of claim 8 further including a control interface disposed on the handle, the control interface operatively associated with the jaw assembly and configured to actuate a transition of the first and second jaw members between the open and clamped configurations, the control interface operatively associated with the light source and configured to activate the light source to emit light from the opening.

10. The surgical instrument of claim 8 further including a display panel disposed on the handle, the display panel operatively associated with the processor and configured to display feedback of the attribute of the tissue.

11. The surgical instrument of claim 8, wherein the processor is disposed within the elongated shaft.

12. The surgical instrument of claim 8, wherein the processor is disposed within the handle.

13. The surgical instrument of claim 8, wherein one of the first and second jaw members includes a staple cartridge, the staple cartridge including a plurality of staples configured to fire through tissue clamped between the first and second jaw members.

14. The surgical instrument of claim 13, wherein the processor is configured to control the firing of staples from the surgical instrument.

15. A method for detecting tissue attributes comprising:
    providing a jaw assembly including first and second jaw members moveable relative to one another between an open configuration and a clamped configuration;
    clamping tissue between the first and second jaw members of the jaw assembly;
    emitting light from an opening in a surface of the first jaw member;
    sensing properties of light reflected off the tissue clamped within the jaw assembly into the opening with a light detector positioned within the opening;
    transmitting signals indicative of the properties of light to a processor;

determining tissue attributes from the signals with the processor; and providing feedback of the tissue attributes to a user.

16. The method of claim 15 further comprising sensing properties of light transmitted through the tissue clamped between the first and second jaw member of the jaw assembly, the first jaw member including a light source and the second jaw member including a second light detector.

17. The method of claim 15, wherein emitting light from the opening includes activating a light source of the first jaw member.

18. The method of claim 15 further comprising firing staples from a staple cartridge coupled to one of the first and second jaw members through tissue clamped between the first and second jaw members.

19. The method of claim 18, wherein determining tissue attributes comprises determining tissue thickness and the method further includes:

comparing the determined tissue thickness to a predetermined tissue thickness value; and preventing additional functions of the surgical instrument when the tissue thickness is greater than the predetermined value.

20. The method of claim 19 further comprising inputting the predetermined tissue thickness value into a control interface operatively associated with the processor.

21. The method of claim 19 further comprising coupling the staple cartridge to one of the first and second jaw members, the staple cartridge transmitting the predetermined value to the processor.

* * * * *